United States Patent [19]

Lalu et al.

[11] Patent Number: 4,610,829
[45] Date of Patent: Sep. 9, 1986

[54] POLYFLUORINATED SULPHONIC ACIDS AND THEIR DERIVATIVES

[75] Inventors: Jean-Pierre Lalu, La Mulatiere; Louis Foulletier, Oullins, both of France

[73] Assignee: Produits Chimiques Ugine Kuhlmann, Courbevoie, France

[21] Appl. No.: 966,508

[22] Filed: Dec. 4, 1978

Related U.S. Application Data

[63] Continuation of Ser. No. 312,880, Dec. 7, 1972, abandoned, which is a continuation of Ser. No. 851,081, Aug. 18, 1969, abandoned.

[30] Foreign Application Priority Data

Aug. 21, 1968 [FR] France .................................. 163.587

[51] Int. Cl.$^4$ ............................................. C07C 143/70
[52] U.S. Cl. ........................... 260/543 R; 106/287.23; 252/33; 252/353; 252/395; 260/513 R; 556/85; 556/177
[58] Field of Search .................................... 260/543 R

[56] References Cited

U.S. PATENT DOCUMENTS

| | | | |
|---|---|---|---|
| 2,732,398 | 1/1956 | Brice | 260/543 |
| 3,130,221 | 4/1964 | Oesterling | |
| 3,810,939 | 5/1974 | Raychauduri | 260/543 |

*Primary Examiner*—Michael L. Shippen
*Attorney, Agent, or Firm*—Pennie & Edmonds

[57] ABSTRACT

New products and compositions of matter complying with the general formula:

$$[C_nF_{2n+1}\text{---}(CH_2)_b\text{---}SO_2\text{---}Z]_dM$$

wherein: $C_nF_{2n+1}$ represents a straight or ramified branched perfluorinated chain: n represents a whole number between 1 and 20, b is a whole number between 2 and 20, preferably equal to 2 or 4, Z represents a chlorine, bromine or an oxygen atom (when Z is a chlorine or a bromine atom, M is nothing and d is equal to 1), when Z is an oxygen atom: M is a hydrogen atom in which case, d is equal to 1, M is a metal of the Groups $I_A$, $II_A$, $I_B$, $II_B$, VIII of the periodic table, the ammonium radical, the aluminum or the lead radical, and in which case d represents the valence of this metal and methods for preparing new products as illustrated by the following representative reactions.

10 Claims, No Drawings

POLYFLUORINATED SULPHONIC ACIDS AND THEIR DERIVATIVES

CROSS REFERENCE TO RELATED APPLICATION

This is a continuation of application Ser. No. 312,880, filed Dec. 7, 1972, now abandoned, which in turn is a continuation of our prior copending application Ser. No. 851,081, filed Aug. 18, 1969, and now abandoned.

SUMMARY OF THE INVENTION

The present invention involves new industrial compounds or products complying with the general formula:

$$[C_nF_{2n+1}-CH_2-_bSO_2-Z]_dM$$

wherein: $C_nF_{2n+1}$ represents a straight or ramified branched perfluorinated chain; n represents a number between 1 and 20, b is a whole number between 2 and 20, preferably equal to 2 or 4, Z represents a chlorine, bromine or an oxygen atom (when Z is a chlorine or a bromine atom, M is nothing and d is equal to 1), when Z is an oxygen atom: M is a hydrogen atom and in which case, d is equal to 1 or M is a metal of the Groups $I_A$, $II_A$, $I_B$, $II_B$, VIII of the periodic table, the ammonium radical, the aluminum or the lead radical and in which case d represents the valence of this metal. The novel compounds are prepared as illustrated by the following representative reactions:

$$C_nF_{2n+1}(CH_2)_bSCN+3Cl_2+2H_2O \rightarrow C_nF_{2n+1}(CH_2)_bSO_2Cl+CNCl+4HCl \quad (1)$$

$$C_nF_{2n+1}(CH_2)_bY+Na_2SO_3 \rightarrow C_nF_{2n+1}(CH_2)_bSO_3Na+NaY \quad (2)$$

wherein Y = Br or I $$C_nF_{2n+1}(CH_2)_bSO_2Cl+2NaOH \rightarrow C_nF_{2n+1}(CH_2)_bSO_3Na+NaCl+H_2O \quad (3)$$

wherein n and b are as represented above.

DESCRIPTION OF THE PREFERRED EMBODIMENT

The preparation of polyfluorinated sulphocyanides $C_nF_{2n+1}(CH_2)_b$ SCN used in reaction (1) has been described in the French patent application PV.138.101 of Jan. 31, 1968, in the applicant's name. The oxidation of a polyfluorinated sulphocyanide having the formula $C_nF_{2n+1}(CH_2)_b$ SCN by the chlorine or the bromine is easily carried out when the sulphocyanide is dissolved in a suitable solvent as a reaction medium. It is preferred to use as a solvent a water-acetic acid mixture containing between 5 and 25% of the water by volume.

A reaction temperature between about 15° and 120° C. can generally be used but it is preferred to use a reaction temperature between 15° and 75°.

During the reaction (1) a by-product is obtained, namely the polyfluoroalkane halide, whose formula is $C_nF_{2n+1}(CH_2)_bX$ wherein X is the chlorine or the bromine. The polyfluorinated sulphocyanide can be regenerated by reaction with an alkaline sulphocyanide according to the reaction:

$$C_nF_{2n+1}(CH_2)_bX+SCN^- \rightarrow C_nF_{2n+1}(CH_2)_bSCN+X^- \quad (4)$$

The following table indicates the boiling and the melting points of some products forming the subject of the invention. Owing to the reactivity of these products, the indicated values may show some inaccuracy.

|  | PE °C. | PF °C. |
|---|---|---|
| $C_2F_5-C_2H_4-SO_2Cl$ | 97°/100 mm |  |
| $C_4F_9-C_2H_4-SO_2Cl$ | 94°/20 mm |  |
| $C_6F_{13}-C_2H_4-SO_2Cl$ | 118-120°/20 mm |  |
| $C_8F_{17}-C_2H_4-SO_2Cl$ | 141°/20 mm | 62.3 |
| $C_{10}F_{21}-C_2H_4-SO_2Cl$ | — | 97–8 |

The action of a mineral sulphite on a polyfluoroalkane halide $C_nF_{2n+1}(CH_2)_bY$ (Y being the iodine or the bromine) as whown in equation (2) above is carried out under the classicial conditions of the Strecker's reaction. The reaction can be carried out in the presence of many solvents such as water, an alcohol (preferably ethanol), a ketone (preferably acetone), or an aprotic solvent (preferably dimethylformamide or dimethylsulphoxide). A mixture of solvents falling in the above classes can be used. It is preferred however, to use a mixture of water and ethanol, volume per volume.

The applicants have also discovered that the addition of a small quantity of copper turnings aids in the nucleophile attack of the polyfluoroalkane halide $C_nF_{2n+1}(CH_2)_bY$ by the sulphite ion.

The reaction can be carried out at a temperature between about 20° and 250° C., preferably between 50° and 150°. If the reaction temperature is above the boiling point of the reaction mixture or one of its constituents, it can be carried out in an autoclave (See Example 9).

The polyfluorinated sulphonates $[C_nF_{2n+1}(CH_2)_bSO_3]_dM$, as set forth in equation (3) above, may also be obtained by neutralizing the halides of polyfluorinated sulphonic acids $C_nF_{2n+1}(CH_2)_bSO_2Z$ with the aid of a base of the formula $M(OH)_d$ where M and d have the meanings designated above. This neutralizing is carried out under the usual conditions for this kind of reaction. The reaction can be carried out in the presence of many solvents, such as water, an ether (such as isopropyl ether), a ketone (such as acetone) or their mixtures. It is preferred, however, to operate in the presence of water. The reaction temperature can be between about 10° and 100° C. but prefereably at about 20° C. An increase in the reaction temperature, although it is not necessary, may accelerate the reaction owing to the solubility.

The new compounds of this invention are useful in the textile industry, and in the leather and paper industries. They can also be employed as corrosion inhibitory agents, surface active agents and levelling agents. The compounds can thus be incorporated in waxes, greases, varnishes and paints to improve the spreading out and levelling of such viscous products.

The following examples illustrate the invention. In all the examples, when a fraction contains several constituents the mentioned percentages are molar percentages of the various compounds and the yields are referred to the starting fluorinated material.

EXAMPLE 1

Chlorine was bubbled to 20°, for 3 h, at the rate of 4 l/h, through a mixture of $C_2F_5-C_2H_4-SCN$ (20.5 g; 0.1 mole), ice acetic acid (100 cm3) and water (12 cm3 at 20° C. for 3 hours at the rate of 4 l/hour. After 1 hour and 45 minutes, the temperature rose to 61° C. in 15 minutes. It remained at this value for 15 minutes and then it gradually went down to the ambient temperature. The chlorine output was then stopped and the apparatus surged with a nitrogen flow for 30 minutes. A solid (4.1 g) was then filtered from the reaction mixture the main constituent or which was ammonium chloride. The filtrate was distilled and 4 fractions and one residue was obtained as follows:

a-Fraction 54°-60°/100 mm, 5.81 g was composed of water and acetic acid b-Fraction 62°-5°/100 mm. Water (100 cm3) was added to this fraction, and a dense phase was decanted (7.6 g) composed of water (2.4%), acetic acid (11.6%) and $C_2F_5$—$C_2H_4$—$SO_2Cl$ (85.8%; 29.6 mmole)

c-Fraction 62°-92°/100 mm; 4.8 g was composed of $C_2F_5$—$C_2H_4$—Cl (1%), acetic acid (70%) and $C_2F_5$—$C_2H_4$—$SO_2Cl$ (29%; 12 mmole)

d-Fraction 92°-7°/100 mm; 6.5 g was composed of $C_2F_5$—$C_2H_4$—Cl (2.8%), $C_2F_5$—$C_2H_4$—$SO_2Cl$ (92.4%; 24.7 mmole) and three unidentified compounds (4.8%)

e-Solid residue, 3.2 g unidentified solid. $C_2F_5$—$C_2H_4$—$SO_2Cl$ was obtained with a conversion rate of 66.5%.

EXAMPLE 2

Chlorine, at the rate of 4 l/hour, was bubbled at 50° C. for 3 hours and 30 minutes through a mixture of $C_4F_9$—$C_2H_4$—SCN (30.5 g; 0.1 mole), icy acetic acid (100 cm3) and water (12 cm3). After 30 minutes, the temperature rose to 75° C. and remained at this value for 30 minutes before gradually going down to the ambient temperature. After stopping the chlorine output, the apparatus was purged with a nitrogen flow for 30 minutes. A solid (3.9 g) was then filtered from the mixture, the main constituent of which was ammonium chloride. The filtrate was distilled two fractions and one residue were obtained:

a-Fraction 50°-64°/100 mm, constituted of water and acetic acid b-Fraction 90°-95°/20 mm; 27.4 g composed of $C_4F_9$—$C_2H_4$—Cl (3.4%), $C_4F_9$—$C_2H_4$—SCN (12.3%/10 mmole) and $C_4F_9$—$C_2H_4$—$SO_2Cl$ (84.3%; 23.6 mmole)

c-Solid residue 4.6 g unidentified solid $C_4F_9$—$C_2H_4$—$SO_2Cl$ was obtained with a conversion rate of 65% and a yield of 75.5%.

EXAMPLE 3

Chlorine, at the rate of 5 l/hour, was bubbled for 2 hours through a mixture of $C_6F_{13}$—$C_2H_4$—SCN (40.5 g; 0.1 mole), icy acetic acid (100 cm3) and water (12 cm3). The reaction vessel was maintained at 63° C. The introduction of the chlorine caused a rise in the temperature to 72° C. after 30 minutes. This temperature remained stable for 30 minutes, then gradually went down to 63° C. The chlorine output was stopped and the apparatus purged with a nitrogen flow for 30 minutes. A mineral solid (4.9 g) was removed from the mixture by filtering, the main component was ammonium chloride. The filtrate was distilled and 4 fractions and one residue were obtained as follows:

a-52°-60°/100 mm; composed of water and acetic acid b-62°-6°/100 mm; 61 g. 50 cm3 of water was added to this fraction, and a dense phase (1.5 g) decanted composed of $C_6F_{13}$—$C_2H_4$—$SO_2Cl$ (68%; 2.4 mmole) and $C_6F_{13}$—$C_2H_4$—Cl (32%)

c-38°-105°/20 mm; 9.2 g; $C_6F_{13}$—$C_2H_4$—Cl (51% $C_6F_{13}$—$C_2H_4$—$SO_2Cl$ (7% 12.6 mmole)

Monochloracetic acid (9.2%), acetic acid (31%)

d-108°-115°/20 mm; 33.4 g; $C_6F_{13}$—$C_2H_4$—$SO_2Cl$ (85.4%; 65 mmole), $C_6F_{13}$—$C_2H_4$—Cl (14.6%; 11 mmole)

e-Residue 1.5 g unidentified. $C_6F_{13}$—$C_2H_4$—$SO_2Cl$ was obtained with a conversion rate of 70% and a yield of 78.5%.

EXAMPLE 4

Chlorine, at the rate of 4 l/hour, was bubbled for 4 hours through a mixture of $C_8F_{17}$—$C_2H_4$—SCN (50.5 g; 0.1 mole), icy acetic acid (100 cm3) and water (12 cm3). The reaction vessel was maintained at 50° C. 15 minutes after introducing chlorine, the temperature rose to 62° C. This temperature remained stable for 1 hour, and gradually went down to 50° C. The chlorine output was then stopped and the apparatus purged with a nitrogen flow for 30 minutes. A solid (52.8 g) was filtered from the reaction mixture and recrystallized in 90 cm3 of carbon tetrachloride. A mineral solid (4 g) was removed by filtration in a hot state and the filtrate cooled down to 20° C., and a solid A (37.2 g) filtered therefrom The last filtrate was concentrated to 20 cm3, which resulted in the precipitation of a solid B (7.4 g) which was filtered therefrom. The solids A and B are identical and comply with the formula $C_8F_{17}$—$C_2H_4$—$SO_2Cl$. $C_8F_{17}$—$C_2H_4$—$SO_2Cl$ was obtained with a conversion rate of 81.5%.

EXAMPLE 5

Chlorine at the rate of 4 l/hour, was bubbled at 75° C. for 2 hours through a mixture of $C_{10}F_{21}$—$C_2H_4$—SCN (30.3 g; 0.05 mole), water (6 cm3) and icy acetic acid (50 cm3). After 30 minutes, the temperature rose to 80° C., and it remained at this value for 45 minutes and then gradually went down to 75° C. After stopping the chlorine output, the apparatus was purged with a nitrogen flow for 30 minutes. A solid (34 g) was filtered from the reaction mixture and recrystallized in 200 cm3 of carbon tetrachloride The solid was collected (29.3 g) which was composed of $C_{10}F_{21}$—$C_2H_4$—$SO_2Cl$ (83%; 38 mmole) and of $C_{10}F_{21}$—$C_2H_4$—SCN (17% 17.8 mmole) $C_{10}F_{21}$—$C_2H_4$—$SO_2Cl$ was obtained with a conversion rate of 76% and a yield of 90%.

EXAMPLE 6

A mixture of $C_2F_5$—$C_2H_4$—I (27.4 g; 0.1 mole), $Na_2SO_3$ (25 g; 0.2 mole), water (50 cm3), ethanol (50 cm3) and a turning of copper (1 g) was maintained at a temperature of 78° C. for 48 hours.

The reaction mixture formed was a liquid and a solid. A solid A (26 g) was obtained therefrom by filtration and washed with 25 cm3 of water. A solid B (17 g) remained. The filtrate was distilled and two fractions and one residue were obtained as follows:

a-49°/200 mm: ethanol b-60°/200 mm: water c-residue

This residue was washed with 10 cm3 of water and separated by filtering a solid C (6 g). The solids B and C were collected and recrystallized in a water-ethanol mixture (50 cm3 per 100 cm3). 20.1 g of $C_2F_5$—$C_2H_4$—$SO_3Na$ were collected which corresponds to a conversion rate of 80%.

EXAMPLE 7

It has been kept to 78° C. for 48 hours. A mixture of $C_4F_9$—$C_2H_4$—I (37.4 g; 0.1 mole), $Na_2SO_3$ (25 g; 0.2 mole), water (50 cm3), ethanol (50 cm3) and a turning of copper (1 g) were maintained at 78° C. for 48 hours in a suitable vessel. The reaction mixture was composed of a liquid and a solid. The solid was filtered therefrom (34.2 g) and washed with 100 cm3 of water before being recrystallized in water (50 cm3). The recrystallization solid was polyfluorinated sulphonate $C_4F_9$—$C_2H_4$—$SO_3Na$, which after drying at 120° C. weighed 17.2 g.

The filtrate was distilled and three fractions were obtained as follows:

a-Fraction 60°/400 mm. This fraction was composed of two phases, they were stirred with 50 cm3 of water and the two phases collected, by decanting, the densest phase (16.2 g) was composed of $C_4F_9$—$C_2H_4$—I (98%; 0.041 mole and ethanol (2%).

b-Fraction 65°/400 mm: ethanol c-Fraction 80°/400 mm: water and few ethanol. $C_4F_9$-$C_2H_4$-$SO_3Na$ was thus recovered with a conversion rate of 49% and a yield of 83%.

EXAMPLE 8

A mixture of $C_6F_{13}$—$C_2H_4$—I (47.4 g; 0.1 mole), $Na_2SO_3$ (25 g; 0.2 mole), water (50 cm3) and ethanol (50 cm3) was maintained at 78° C. for 48 hours in a suitable reaction vessel. The reaction mixture resulting was a liquid and a solid. The solid was filtered therefrom and washed with 100 cm3 of water, and after filtering, the solid was dried in a drying vessel at 120° C., 20 g of $C_6F_{13}$—$C_2H_4$—$SO_3Na$ were thus obtained.

The filtrate was distilled and one fraction and one residue were obtained as follows:

a-Fraction 49°/200 mm: ethanol b-Residue. This residue contained water and a solid. The solid (0.9 g) was filtered and was the sulfonate $C_6F_{13}$—$C_2H_4$—$SO_3Na$. The filtrate was evaporated and a solid (4.1 g) whose origin is mainly mineral was obtained.

$C_6F_{13}$—$C_2H_4$—$SO_3Na$ was thus obtained with a conversion rate of 46.5%.

EXAMPLE 9

A mixture of $C_6F_{13}$—$C_2H_4$—I (47.4 g: 0.1 mole), $Na_2SO_3$ (25 g: 0.2 mole), water (50 cm3), ethanol (50 cm3) and a turning of copper (1 g) was maintained at 120° C. for 48 hours in an autoclave. The maximum pressure was 3 bars. After cooling down the autoclave to 20° C., the reaction mixture was composed of a liquid and a solid. The solid was filtered and weighed 53 g. The solid was washed with 100 cm3 of water and after filtering, it was recrystallized in one liter of water. The solid collected (35 g) was the polyfluorinated sulphonate $C_6F_{13}$-$C_2H_4$-$SO_3Na$; the conversion rate amounted to 78%.

EXAMPLE 10

A mixture of $C_6F_{13}$-($C_2H_4$)$_2$I (25 g; 0.05 mole), $Na_2SO_3$ (12.5 g; 0.1 mole), water (25 cm3), ethanol (25 cm3) and a turning of copper (0.5 g) was maintained at 85° C. for 48 hours. The reaction mixture was composed of a liquid and a solid, and the solid was filtered therefrom. The solid weighed 28 g and was washed with 50 cm3 of water and recrystallized in ethanol (300 cm3). The solid collected (19.2 g) was the polyfluorinated sulphonate $C_6F_{13}$-($C_2H_4$)-$SO_3Na$ the conversion rate was 80%.

EXAMPLE 11

20 cm3 of NaOH (10N) were rapidly added to $C_8F_{17}$—$C_2H_4$—$SO_2Cl$ (10.93 g; 0.02 mole). During this addition, the temperature rose from 20° to 45° C. The mixture was then brought to and maintained at 100° C. for 4 hours. A solid was recovered therefrom by filtering. This solid was washed with water (3×20 cm3), dried and collected. This solid (10.9 g) was the polyfluorinated sulphonate $C_8F_{17}$—$C_2H_4$—$SO_3Na$. The conversion rate amounted to 99%.

EXAMPLE 12

A mixture of $C_6F_{13}$—$C_2H_4$—$SO_2Cl$ (11.16 g; 0.025 mole), water (40 cm3) and sulphuric acid at 66° C. B (12 g) was maintained at 100 C. for 8 hours. The mixture was then extracted with ethyl ether (4×50 cm3) and the ether eliminated or removed by distillation. The resulting residual solid was dried under vacuum. The dry solid obtained (8.8 g) was the sulphonic acid $C_6F_{13}$—$C_2H_4$—$SO_3H$ melting between 73° and 79° C. The conversion rate was 82.5%.

We claim:

1. A product having the formula $C_nF_{2n+1}(CH_2)_b$—$SO_2$—Z wherein $C_nF_{2n+1}$ represents a straight or branched perfluorinated hydrocarbon chain, n is a number between 1 and 20, b is a number between 2 and 20 and Z is a chlorine or bromine atom.

2. A product according to claim 1 in which b is 2 or 4.

3. A product according to claim 1 in which b is 2.

4. A product according to claim 3 in which Z is chlorine.

5. A product according to claim 3 in which Z is bromine.

6. A product according to claim 4 in which n is a number between 2 and 10.

7. A product according to claim 6 in which n is the number 2.

8. A product according to claim 6 in which n is the number 4.

9. A product according to claim 6 in which n is the number 6.

10. A product according to claim 6 in which n is the number 10.

* * * * *